US009161747B2

(12) United States Patent
Whittaker et al.

(10) Patent No.: US 9,161,747 B2
(45) Date of Patent: Oct. 20, 2015

(54) COMPRESSION EXPANDED CANNULA

(71) Applicant: DePuy Mitek, LLC, Raynham, MA (US)

(72) Inventors: Gregory R. Whittaker, Stoneham, MA (US); Gary McAlister, Franklin, MA (US); Jason Hamilton, Dartmouth, MA (US)

(73) Assignee: DePuy Mitek, LLC, Raynham, MA (US)

( * ) Notice: Subject to any disclaimer, the term of this patent is extended or adjusted under 35 U.S.C. 154(b) by 242 days.

(21) Appl. No.: 13/861,831

(22) Filed: Apr. 12, 2013

(65) Prior Publication Data

US 2013/0303858 A1 Nov. 14, 2013

Related U.S. Application Data

(63) Continuation of application No. 12/030,590, filed on Feb. 13, 2008, now abandoned.

(51) Int. Cl.
*A61B 17/00* (2006.01)
*A61B 17/02* (2006.01)
*A61B 17/34* (2006.01)

(52) U.S. Cl.
CPC ......... *A61B 17/0218* (2013.01); *A61B 17/3421* (2013.01); *A61B 17/3439* (2013.01); *A61B 2017/349* (2013.01); *A61B 2017/3419* (2013.01); *A61B 2017/3484* (2013.01)

(58) Field of Classification Search
CPC ........... A61B 17/0218; A61B 17/3421; A61B 17/3439; A61B 2017/3419; A61B 2017/3484; A61B 2017/349
See application file for complete search history.

(56) References Cited

U.S. PATENT DOCUMENTS

| 3,344,791 | A | 10/1967 | Foderick |
| 3,970,090 | A | 7/1976 | Loiacono |
| 4,430,081 | A | 2/1984 | Timmermans |
| 4,475,548 | A | 10/1984 | Muto |

(Continued)

FOREIGN PATENT DOCUMENTS

| EP | 1774918 | 4/2007 |
| EP | 1908428 | 4/2008 |

(Continued)

*Primary Examiner* — Aarti B Berdichevsky

(57) ABSTRACT

Various methods and devices are provided for accessing an interior surgical site using an access portal which can be inserted and removed with minimal tissue damage and which can form a seal with tissue while inserted. Generally, a device is provided having a rigid elongate surgical access member with a lumen extending therethrough that is configured to receive a surgical tool. The device can also include a flexible sleeve having a lumen extending therethrough that is configured to receive the elongate surgical access member. A substantially rigid collar is provided disposed adjacent to a proximal end of the flexible sleeve and having a lumen extending therethrough that is configured to receive the elongate surgical access member. In an exemplary embodiment, the collar is movable relative to the elongate surgical access member to selectively configure the flexible sleeve in a relaxed condition in which the flexible sleeve has a relatively smooth outer tissue-contacting surface and a compressed condition in which the flexible sleeve has a plurality of protrusions formed on the outer tissue-contacting surface that are configured to create a seal between the outer tissue-contacting surface and tissue.

8 Claims, 11 Drawing Sheets

(56) References Cited

U.S. PATENT DOCUMENTS

| | | | |
|---|---|---|---|
| 4,655,752 A | 4/1987 | Honkanen | |
| 5,053,013 A | 10/1991 | Ensminger | |
| 5,176,652 A | 1/1993 | Littrell | |
| 5,197,971 A | 3/1993 | Bonutti | |
| 5,203,773 A | 4/1993 | Green | |
| 5,207,656 A | 5/1993 | Kranys | |
| 5,273,545 A | 12/1993 | Hunt | |
| 5,290,249 A | 3/1994 | Foster | |
| 5,443,449 A | 8/1995 | Buelna | |
| 5,478,329 A | 12/1995 | Ternamian | |
| 5,643,227 A | 7/1997 | Stevens | |
| 5,779,697 A | 7/1998 | Glowa | |
| 5,836,913 A | 11/1998 | Orth | |
| 5,857,999 A | 1/1999 | Quick | |
| 5,888,196 A | 3/1999 | Bonutti | |
| 6,123,689 A | 9/2000 | To | |
| 6,210,397 B1 | 4/2001 | Aboul-Hosn | |
| 6,432,085 B1 | 8/2002 | Stellon | |
| 6,450,992 B1 | 9/2002 | Cassidy, Jr. | |
| 6,610,031 B1 | 8/2003 | Chin | |
| 6,613,062 B1 | 9/2003 | Leckrone | |
| 6,632,179 B2 | 10/2003 | Wilson | |
| 6,632,197 B2 * | 10/2003 | Lyon | 604/107 |
| 6,695,816 B2 | 2/2004 | Cassidy, Jr. | |
| 6,837,871 B2 | 1/2005 | Gonzales | |
| 7,235,064 B2 | 6/2007 | Hopper | |
| 7,311,719 B2 | 12/2007 | Bonutti | |
| 8,157,833 B2 * | 4/2012 | Au et al. | 606/191 |
| 2001/0049502 A1 | 12/2001 | Chen | |
| 2002/0193806 A1 | 12/2002 | Moenning | |
| 2003/0009175 A1 | 1/2003 | Cassidy | |
| 2003/0093104 A1 | 5/2003 | Bonner | |
| 2003/0167069 A1 | 9/2003 | Gonzales | |
| 2003/0195472 A1 | 10/2003 | Green | |
| 2004/0024435 A1 | 2/2004 | Leckrone | |
| 2004/0034364 A1 | 2/2004 | Snyder | |
| 2005/0119685 A1 | 6/2005 | Smith | |
| 2005/0209607 A1 | 9/2005 | Lipchitz | |
| 2006/0079925 A1 | 4/2006 | Kerr | |
| 2006/0212062 A1 | 9/2006 | Farascioni | |
| 2007/0032703 A1 | 2/2007 | Sankaran | |
| 2007/0060939 A1 | 3/2007 | Lancial | |
| 2007/0106319 A1 * | 5/2007 | Au et al. | 606/191 |
| 2007/0162066 A1 | 7/2007 | Lyon | |
| 2008/0058716 A1 * | 3/2008 | Dubrul et al. | 604/104 |
| 2008/0058723 A1 | 3/2008 | Lipchitz | |
| 2008/0065140 A1 | 3/2008 | Bonutti | |
| 2008/0086165 A1 | 4/2008 | Lyon | |
| 2010/0185058 A1 * | 7/2010 | Mastri et al. | 600/204 |
| 2012/0143141 A1 * | 6/2012 | Verkaik et al. | 604/175 |
| 2014/0309592 A1 * | 10/2014 | Melvin et al. | 604/164.11 |

FOREIGN PATENT DOCUMENTS

| | | |
|---|---|---|
| FR | 2810555 | 12/2001 |
| WO | 9420026 | 9/1994 |
| WO | 9742870 | 11/1997 |
| WO | 9851214 | 11/1998 |
| WO | 0101871 | 1/2001 |
| WO | 2005037079 | 4/2005 |
| WO | 2005092217 | 10/2005 |
| WO | 2008043038 | 4/2008 |

* cited by examiner

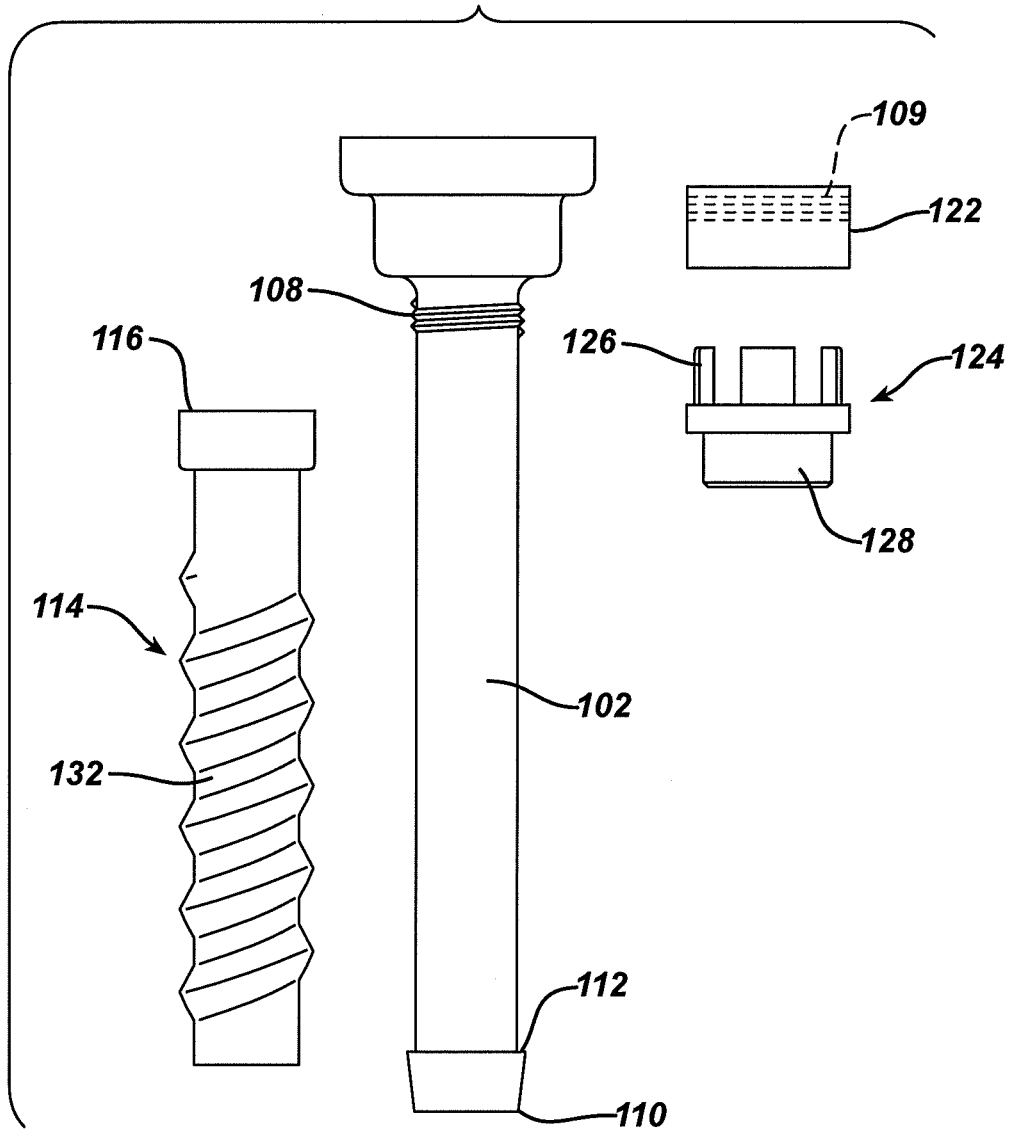

COMPRESSION EXPANDED CANNULA

CROSS REFERENCE TO RELATED APPLICATIONS

This application is a continuation application of U.S. patent application Ser. No. 12/030,590, entitled COMPRESSION EXPANDED CANNULA, filed Feb. 13, 2008, which is incorporated herein by reference.

FIELD

The present invention generally relates to methods and devices for providing access portals through which surgical instruments can be inserted. More particularly, the invention relates to devices which can be inserted into and removed from a patient with minimal tissue damage.

BACKGROUND

Arthroscopic, or more generally, minimally invasive surgical procedures rely on obtaining percutaneous access to an internal surgical site using small-diameter openings to gain access to the desired surgical site. In many cases, access tubes are placed through the opening to allow a variety of elongated instruments to be passed through the access tubes to gain access to an internal surgical work site without the need for large incisions. As a result, patient trauma and recovery time are typically reduced.

Very often, these access tubes, which are often called cannulas, must be left in an incision for an extended period of time, without significant movement, as instruments are inserted and removed. This typically requires rigid surface features on the exterior of the cannula, such as corrugations or threads, to engage the tissue surrounding the cannula. These rigid surface features, however, can cause tissue damage as the cannula is inserted and usually do not result in the most secure fit once in place due to tissue trauma surrounding the cannula. The cannula can also be difficult to remove once inserted due to the rigid surface features, possibly leading to further tissue damage during removal.

Accordingly, there is a need for improved devices and methods that provide access portals which can be inserted into and removed from an incision with minimal tissue damage and can effectively engage tissue while within the incision.

SUMMARY OF THE INVENTION

The present invention generally provides access portals through which surgical procedures can be performed and that can be inserted and removed with minimal tissue damage to form a seal with tissue while inserted. In one embodiment, a surgical access device is provided having an elongate surgical access member with a lumen extending therethrough that is configured to receive a surgical tool. The surgical access device can also include a tubular flexible sleeve having a lumen extending therethrough that is configured to receive the elongate surgical access member. A substantially rigid collar member can be disposed adjacent to a proximal end of the flexible sleeve having a lumen extending therethrough that is configured to receive the elongate surgical access member. In an exemplary embodiment, the collar member is movable relative to the elongate surgical access member to selectively configure the flexible sleeve in a relaxed condition in which the flexible sleeve has a relatively smooth outer tissue-contacting surface and a compressed condition in which the flexible sleeve has a plurality of protrusions formed on the outer tissue-contacting surface that are configured to create a seal between the outer tissue-contacting surface and tissue. The flexible sleeve is normally in the relaxed condition and is configured to receive a compressive force to be configured in the compressed condition.

In an exemplary embodiment, the plurality of protrusions are configured to increase an outer diameter of the flexible sleeve in the compressed condition and can be threads and/or ribs. In addition, the collar member can include threads formed on an interior surface thereof which are configured to mate to corresponding threads formed on an exterior surface of the elongate surgical access member. In one exemplary embodiment, the collar member is configured to rotate via the mated threads and to move the flexible sleeve distally into the compressed condition. The surgical access device can further include at least one camming member in communication with the rigid collar member where the camming member is rotatable to configure the flexible sleeve in a compressed condition. In another exemplary embodiment, the elongate surgical access member can be a cage member coupled between the rigid collar member and a distal ring, where the rigid collar member is effective to move the cage member proximally to configure the flexible sleeve in a compressed condition.

In a further embodiment, a surgical access device is provided having a body defining a central longitudinal axis and a deformable surgical access member configured to be in communication with the body. The deformable surgical access member can define an outer tissue-contacting surface such that the deformable surgical access member is configured to receive a compressive force to effect an increase in an outer diameter thereof to configure the outer tissue-contacting surface in a condition effective to form a seal with tissue. In one exemplary embodiment, the outer tissue-contacting surface can contain threads configured to form a seal with tissue when a compressive force is applied to the deformable surgical access member.

In an embodiment, the deformable surgical access member is disposed between a substantially rigid band disposed adjacent to a proximal end of the deformable surgical access member and a substantially rigid distal ring. The substantially rigid band can include threads formed on an interior surface thereof which are configured to mate with corresponding threads formed on an exterior surface of the body. The substantially rigid band can be configured to rotate via the mated threads to move the substantially rigid band distally and to cause the outer tissue-contacting surface of the deformable surgical access member to form a seal with tissue. In another embodiment, the elongate surgical access member can be a cage member and the substantially rigid band can be configured to rotate via the mated threads to move the cage member proximally to cause the outer tissue-contacting surface of the deformable surgical access member to form a seal with tissue.

Methods are also provided relating to instrument access within a patient and include providing a cannula assembly having a elongate surgical access member with a bore formed therethrough configured to receive a surgical tool. The method can also include inserting the cannula assembly into an incision in a patient in an insertion condition in which a tubular flexible sleeve has a relatively smooth exterior surface and applying a compressive force to the flexible sleeve to move the flexible sleeve from the insertion condition to a compressed condition in which the exterior surface of the flexible sleeve includes surface features which extend radially outward from the elongate surgical access member to form a seal with tissue. In an embodiment, an outer diameter of the flexible sleeve is greater in the compressed condition than in the insertion condition.

The method can further include inserting at least one surgical tool through the bore in the elongate surgical access member to effect a surgical procedure. In an embodiment, the compressive force is applied by sliding a member distally relative to the elongate surgical access member. In another embodiment, the compressive force is applied by rotating at least one camming member. In addition, the compressive force can be applied by withdrawing a surgical tool from the elongate surgical access member and the flexible sleeve, where the compressed condition is the natural state of the flexible sleeve.

BRIEF DESCRIPTION OF THE DRAWINGS

The invention will be more fully understood from the following detailed description taken in conjunction with the accompanying drawings, in which:

FIG. 1C is an exploded view of the device of FIG. 1A;

DETAILED DESCRIPTION

Figure 1A:
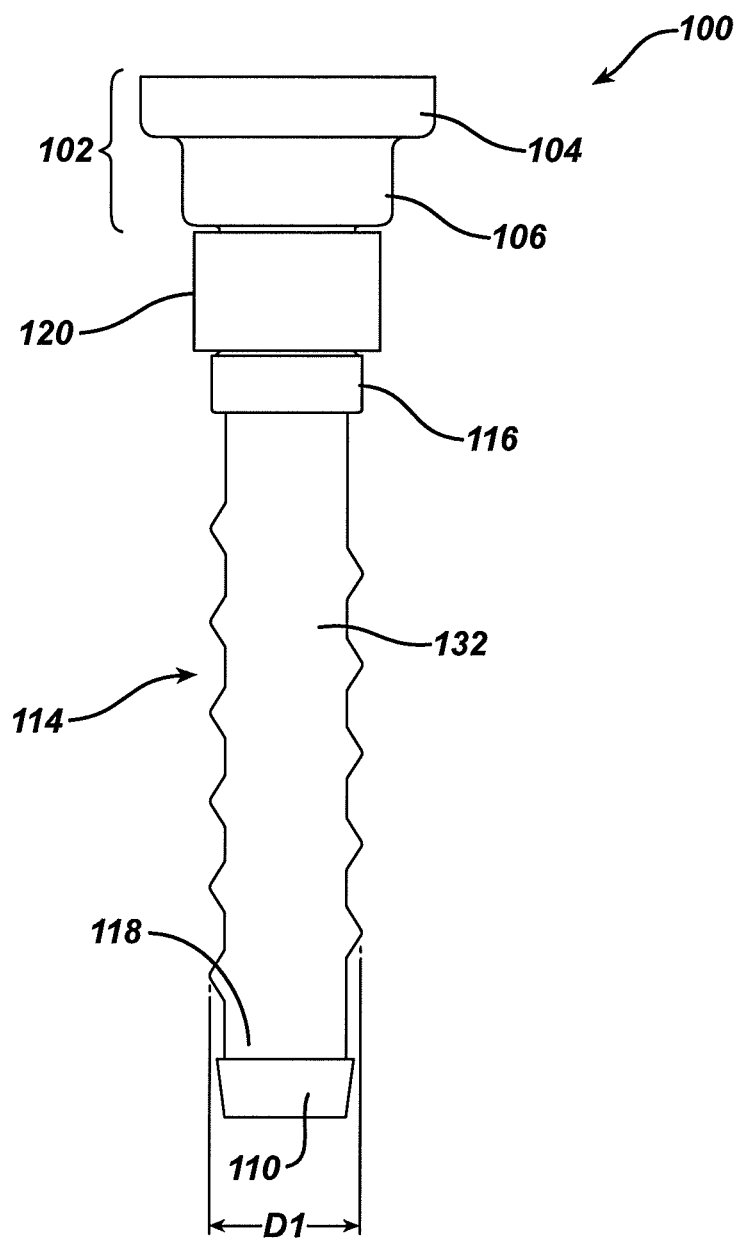
FIG. 1A is a front view of one embodiment of a surgical access device in a relaxed condition.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present application.

The present application provides methods and devices useful for accessing an interior surgical site using an access portal which can be inserted and removed with minimal tissue damage and which can form a seal with tissue while inserted. In an embodiment illustrated in FIGS. 1A-1C, a surgical access device 100 is provided having an elongate surgical access member 102 with a generally cylindrical body and a bore formed therethrough configured for receiving a surgical tool or other device. A proximal most end of the elongate surgical access member 102 can include two flange portions, a first flange portion 104 and a second flange portion 106, each of which have a larger diameter that the elongate surgical access member 102. As will be appreciated by those skilled in the art, the elongate surgical access member 102 and the first and second flanges 104, 106 can be configured to seat and receive surgical tools, valve systems, trocars, obturators, vacuum systems and any other devices that may aid in a surgical procedure. Threads 108 can be formed on an exterior surface of the elongate surgical access member 102, and while the threads 108 can be formed at any location along a length of the elongate surgical access member 102, in the illustrated embodiment, they are formed on a proximal portion of the elongate surgical access member 102 situated at a distance below the second flange 106. The threads 108 are configured to mate with corresponding threads on a substantially rigid collar, as will be described in detail below. A tapered portion 110 can be formed on a distal most end of the elongate surgical access member 102. As will be appreciated by a person skilled in the art, the size of the tapered portion 110 and the amount of tapering can vary depending on the surgical tools expected to be received by the device. A proximal portion of the tapered portion 110 can also include a lip 112 which has a diameter greater than a diameter of the elongate surgical access member 102. In an exemplary embodiment, the lip 112 can seat and/or mate to a distal portion of a deformable surgical access member or flexible sleeve 114 as will be described in detail below. As will be appreciated by those skilled in the art, the elongate surgical access member 102 can be rigid, flexible, and/or semi-rigid and can be formed from a variety of biocompatible materials, including but not limited to polycarbonate, ABS, polyetheretherketone (PEEK), polyetherimide, polystyrene, polyvinylchloride, polyester, polypropelene, polyethelene, polyurethane. One of ordinary skill in the art will appreciate that other polymers or blends thereof may be used to achieve similar properties.

Figure 1B:
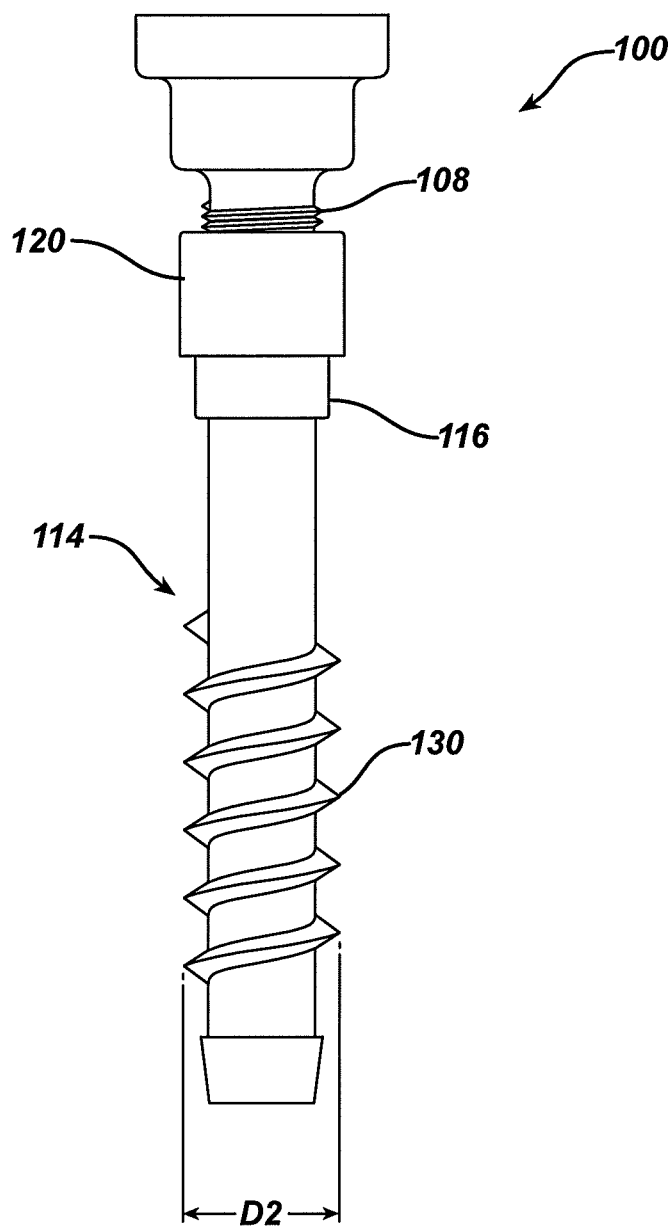
FIG. 1B is a front view of the device of FIG. 1A, in a compressed condition.

In the embodiment illustrated in FIGS. 1A-1C, the substantially rigid collar is in the form of a two-part rotatable bushing 120 divided into a ring 122 and a nut 124. The ring 122 can include threads formed on an interior surface thereof which are configured to mate with the corresponding threads 108 formed on the exterior surface of the proximal portion of the elongate surgical access member 102, as described above. The ring 122 can also be configured to mate with the nut 124 by way, for example, of a press fit or sliding fit, so that the ring 122 can be rotated with respect to the nut 124. The nut 124 can include a proximal male portion 126 configured to seat the ring 122 and a distal male portion 128 configured to mate with a flange 116 formed on a proximal end of the flexible sleeve 114. In this way, the ring 122 can be rotated via the mated threads with respect to both the nut 124 and the flexible sleeve 114. As noted above, the bushing 120 can be substantially rigid and can be formed from a variety of biocompatible materials, including but not limited to polycarbonate, ABS, polyetheretherketone (PEEK), polyetherimide, polystyrene, polyvinylchloride, polyester, polypropelene, polyethelene, polyurethane. One of ordinary skill in the art will appreciate that other polymers or blends thereof may be used to achieve similar properties.

The flexible sleeve 114 can be a substantially tubular member which can be configured to receive the elongate surgical access member 102 within a bore formed therein. In one embodiment, illustrated in FIGS. 1A-1C, a distal most end 118 of the flexible sleeve 114 rests on the lip 112 of the elongate surgical access member 102 and is mated thereto so that the distal most end 118 of the flexible sleeve 114 cannot be moved relative to the elongate surgical access member 102. The flange 116 on the proximal most end of the flexible sleeve 114 can be coupled to the distal male portion 128 of the bushing 120, and can be configured to be movable with the bushing 120 relative to the elongate surgical access member 102. The flexible sleeve 114 is deformable and can be formed from a variety of biocompatible materials, including but not limited to polyvinylchloride, polyurethane, silicone, polyetherimide, polyeetherester, thermoplastic polyolefins. One of ordinary skill in the art will appreciate that other polymers or blends thereof may be used to achieve similar properties.

The flexible sleeve is designed to be selectively configured in a relaxed condition and in a compressed condition. In the relaxed condition, which is the normal or natural state of the flexible sleeve 114, an outer tissue-contacting surface 132 of the flexible sleeve 114 has a relatively smooth surface, as shown in FIG. 1A, with a first diameter D1. While the flexible sleeve 114 can be configured in many different ways, in one embodiment, in the relaxed condition, the flexible sleeve 114 is configured to fit relatively tightly around an outer tissue-contacting surface of the elongate surgical access member 102. Accordingly, in one exemplary embodiment, in the relaxed condition, the difference between the outer diameter of the elongate surgical access member 102 and the first diameter of the flexible sleeve 114 is essentially the thickness of the flexible sleeve 114 itself.

In an embodiment in which the flexible sleeve 114 is configured to be in the compressed condition, a plurality of protrusions 130 can form on the outer surface of the flexible sleeve 114. In the illustrated embodiment, the plurality of protrusions 130 are in the form of threads which are disposed on a distal portion of the flexible sleeve 114. A person skilled in the art will appreciate, however, that the protrusions 130 can also be ridges, threads, ribs or other surface irregularities which can be formed over the entire outer surface of the flexible sleeve 114, or over only a very particular area of the outer surface 132. Therefore, if the flexible sleeve 114 is configured in a compressed condition, the outer surface 132 of the flexible sleeve 114 has a second diameter D2 shown in FIG. 1B, measured from the outermost boundary of the protrusions 130, which is greater than the first diameter D1. In an exemplary embodiment, the first diameter D1 in the relaxed condition can be in the range of about 1 to 5 mm, and more preferably in the range of about 2 to 3 mm. In the compressed condition, the second diameter D2 can be in the range of about 2 to 10 mm, and more preferably in the range of about 4 to 6 mm. A person skilled in the art will appreciate that the device 100 can have any first and second diameter necessary for a particular procedure, or to accommodate any size surgical tool as needed. The protrusions 130 can engage and form a seal with tissue when the device 100 is in the compressed condition.

In one embodiment, the protrusions 130 in the flexible sleeve 114 can be pre-formed in the material of the flexible sleeve 114 so that the outer surface 132 remains relatively smooth in the relaxed condition, and threads, ribs, or other surface irregularities will form when the flexible sleeve 114 is configured in the compressed condition. A person skilled in the art will appreciate the various ways that the protrusions 130 can be pre-formed in the flexible sleeve 114.

In an exemplary embodiment, in use, the device 100 can be inserted into an incision in a patient in an insertion condition in which the flexible sleeve 114 is in a relaxed condition such that the outer surface 132 of the flexible sleeve 114 is relatively smooth. After the device 100 is inserted and positioned as needed within the patient, the ring 122 can be rotated, for example, in a clockwise direction, via the mated threads to configure the flexible sleeve in a compressed condition as the nut 124 and the flexible sleeve 114 are moved in a distal direction. As this action moves the flexible sleeve 114 in a distal direction, the flexible sleeve 114 is compressed between the nut 124 and the lip 112 formed on the tapered portion 110 of the elongate surgical access member 102 so as to cause protrusions 130 to form in the outer surface 132 of the flexible sleeve 114. The protrusions 130 can be configured to engage tissue to prevent pullout and/or movement and to form a seal with the surrounding tissue. Surgical instruments can be inserted and removed through the bore in the elongate surgical access member 102 to perform surgical procedures as needed. At a point in time when the device 100 is no longer needed within the patient, the ring 122 can be rotated in an opposite direction, for example, counter-clockwise, via the mated threads to cause the nut 124 and the flexible sleeve 114 to move in a proximal direction. As the flexible sleeve 114 is moved proximally, the protrusions 130 in the flexible sleeve 114 disengage from sealing contact with the surrounding tissue and essentially disappear as the compression is removed from the flexible sleeve 114 so that the outer surface 132 of the flexible sleeve 114 is relatively smooth and in the relaxed or insertion condition. The device 100 can then be removed from the incision with minimal tissue damage.

Figure 2A:
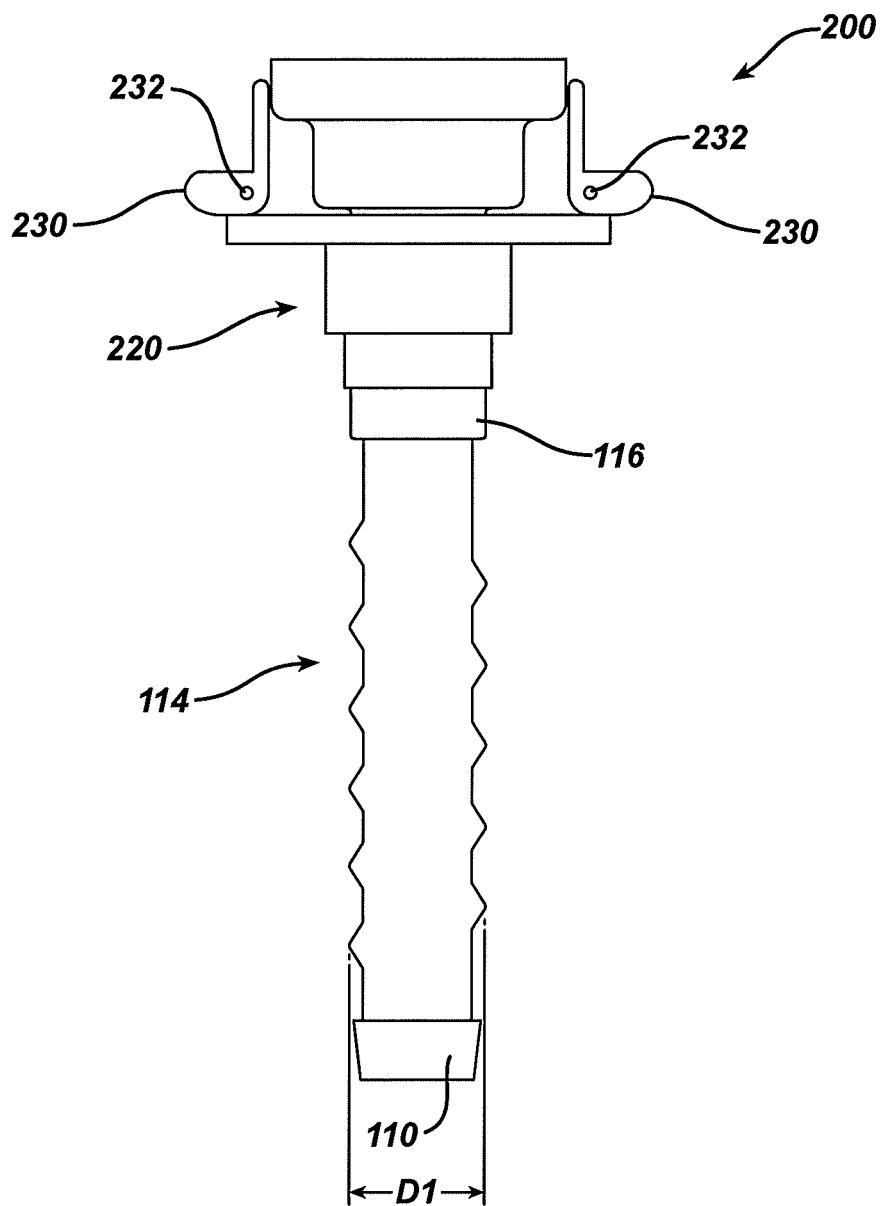
FIG. 2A is a front view of another embodiment of a surgical access device in the relaxed condition.
Figure 2B:
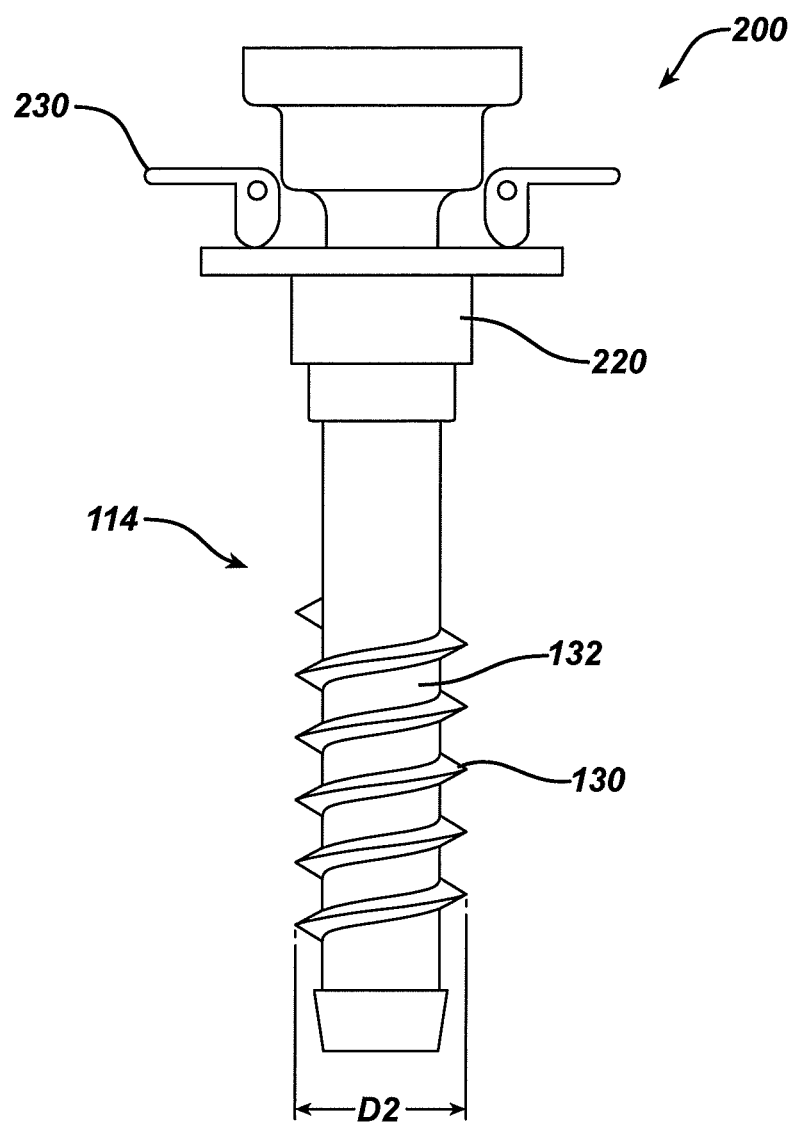
FIG. 2B is a front view of the device of FIG. 2A, in the compressed condition.
Figure 2C:
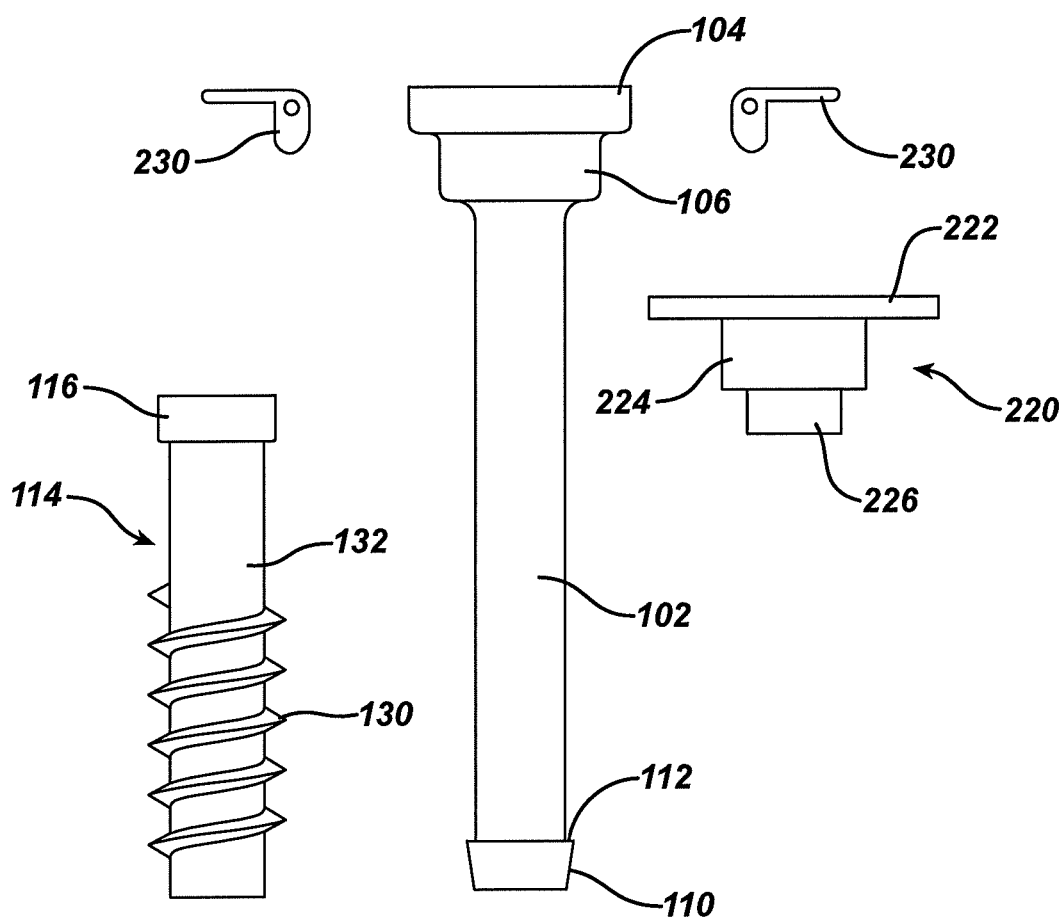
FIG. 2C is an exploded view of the device of FIG. 2A.

In another embodiment, shown in FIGS. 2A-2C, an access device 200 is provided having the rigid elongate surgical access member 102 and flexible sleeve 114 as described above. In addition, the device 200 can include an activation mechanism for configuring the flexible sleeve 114 in the relaxed condition and the compressed condition. The activation mechanism can include a slider member 220 having a bore formed therethrough for receiving the elongate surgical access member 102 and at least one camming member. In the illustrated embodiment, the activation mechanism includes two camming members 230. The slider member 220 can include a proximal flange 222, a base portion 224, and a male mating portion 226 configured to mate with the flange 116 formed on the proximal end of the flexible sleeve 114. The slider member 220 can be configured in many ways, but in the illustrated embodiment, the slider member 220 is adapted to slide relative to the elongate surgical access member 102. In an exemplary embodiment, the camming members 230 are rotatable members coupled to a proximal portion of the elongate surgical access member 102 and are configured to rotate via pins 232 or other connection means known in the art. The camming members 230 are disposed adjacent to the proximal flange 222 of the slider member 220 and are adapted to act upon the proximal flange 222 when the activation mechanism is activated to configure the flexible sleeve 114 in a relaxed condition or a compressed condition, as will be described below.

In an exemplary embodiment, in use, the device 200 can be inserted into an incision in a patient in an insertion condition in which the flexible sleeve 114 is in a relaxed condition such that the outer surface 132 of the flexible sleeve 114 is relatively smooth, as shown in FIG. 2A. After the device is inserted and positioned as needed within the patient, the camming members 230 can be rotated, such as by ninety degrees, as shown in FIG. 2B to cause the slider member 220 to move in a distal direction. As the slider member 220 moves in a distal direction, the proximal end of the flexible sleeve 114 is also moved distally so as to compress the flexible sleeve 114 between the slider member 220 and the lip 112 formed on the tapered portion 110 of the elongate surgical access member 102 and configure the flexible sleeve 114 in a compressed condition. As the flexible sleeve 114 is compressed, protrusions 130 form on the outer surface 132 of the flexible sleeve 114 to engage and form a seal with the surrounding tissue, thereby preventing movement and pullout of the device 200 from the incision. Surgical instruments can be inserted and removed through the bore in the elongate surgical access member 102 to perform surgical procedures as needed. At a point in time when the device is no longer needed within the patient, the camming members 230 can be rotated ninety degrees in the opposite direction, as shown in FIG. 2A, to cause the slider member 220 and the proximal end of the flexible sleeve 114 to move in a proximal direction. As the flexible sleeve 114 is moved proximally, the protrusions 130 in the flexible sleeve 114 disengage with the surrounding tissue and disappear as the compression is removed from the flexible sleeve 114 so that the outer surface 132 of the flexible sleeve 114 is relatively smooth and in the relaxed condition. The device 200 can be removed from the incision with minimal tissue damage.

Figure 3A:
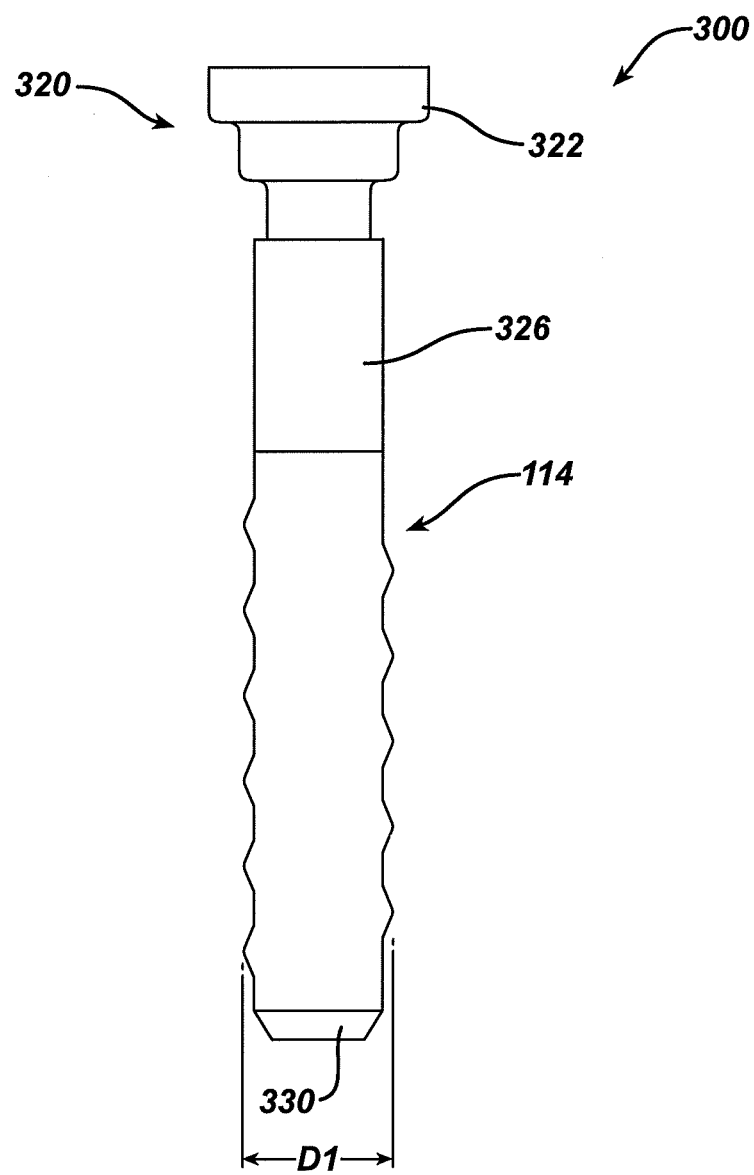
FIG. 3A is a further embodiment of a surgical access device in the relaxed condition.
Figure 3B:
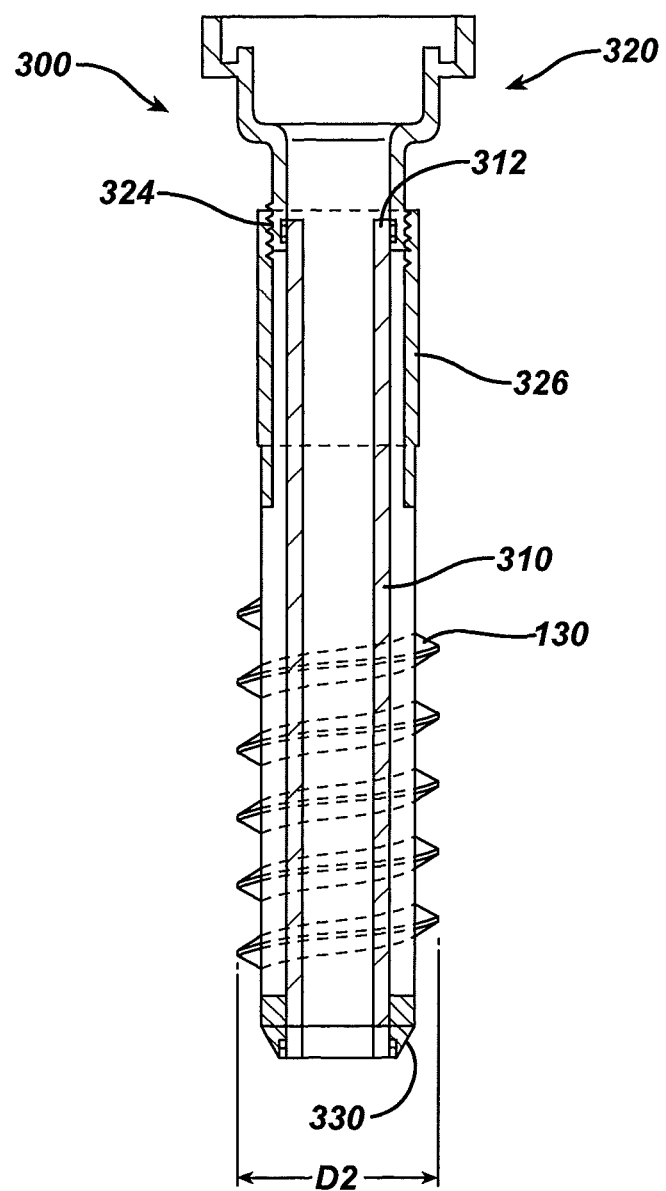
FIG. 3B is a cross-section of the device of FIG. 3A, showing the compressed condition.
Figure 3C:
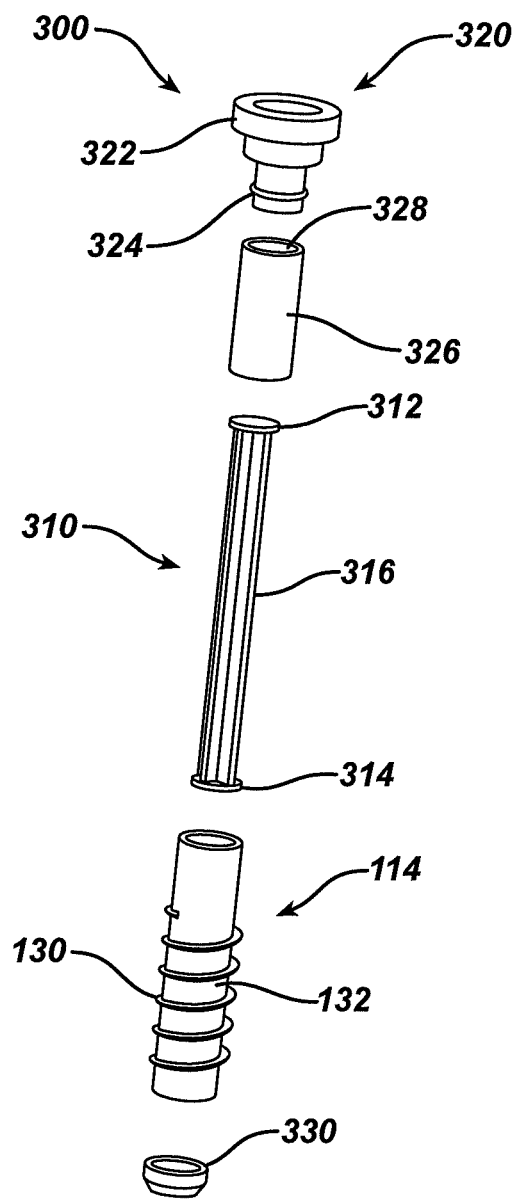
FIG. 3C is an exploded view of the device of FIG. 3A.

In a further embodiment, shown in FIGS. 3A-3C, a device 300 is provided having a cage member 310 coupled to a receiver body 320. The cage member 310 can include a proximal ring 312 that can be rigidly mated with an interior surface of the receiver body 320 by any means known in art, for example a snap fit, press fit, or adhesive. The receiver body 320 and the cage member 310 can have a bore formed therethrough for receiving a surgical tool or other instrument. In an exemplary embodiment, the receiver body 320 can include a proximal flange 322 and a threaded male portion 324 adapted to mate with a corresponding threaded female portion 328 of a substantially rigid collar 326. The rigid collar 326 can have a bore formed therethrough that is configured to receive the cage member 310 when the rigid collar 326 is threadedly mated with the receiver body 320. The cage member 310 can also include about 2 to 10, and more preferably about 4 to 6, vertical bars 316 extending from the proximal ring 312 to a distal ring 314 to form the cage-like structure of the cage member 310. The distal ring 314 of the cage member 310 can be configured to mate with a distal compression member 330 by any means known in the art such as a press fit, a snap fit, or adhesive. A flexible sleeve 114 is disposed between a distal end of the rigid collar 326 and a proximal surface of the distal compression member 330 and includes a bore formed therethrough for receiving the cage member 310.

In an exemplary embodiment, in use, the device 300 can be inserted into an incision in a patient in an insertion condition in which the flexible sleeve 114 is in a relaxed condition such that the outer surface 132 of the flexible sleeve 114 is relatively smooth, as shown in FIG. 3A. After the device 300 is inserted and positioned as needed within the patient, the receiver body 320 can be rotated via the mated threads "out" of the rigid collar 326 to move in a proximal direction. As the receiver body 320 is moved proximally, the cage member 310 and the distal compression member 330 are both pulled proximally, thereby compressing the flexible sleeve 114 between the rigid collar 326, which is not moving, and the distal compression member 330. As the flexible sleeve 114 is compressed, protrusions 130 form on the outer surface 132 thereof to engage and form a seal with the surrounding tissue, thereby preventing movement and pullout of the device 300 from the incision. Surgical instruments can be inserted and removed through the bore in the elongate surgical access member 102 to perform surgical procedures as needed. At a point in time when the device 300 is no longer needed within the patient, the receiver body 320 can be rotated via the mated threads back "into" the rigid collar 326 to move in a distal direction, thereby moving the cage member 310 and the distal compression member 330 distally. As the distal compression member 330 is moved distally, the flexible sleeve 114 disengages from a seal with the surrounding tissue and returns to the insertion or relaxed condition as the compression is removed to have a relatively smooth outer surface 132. The device 300 can then be removed from the incision with minimal tissue damage.

Figure 4A:
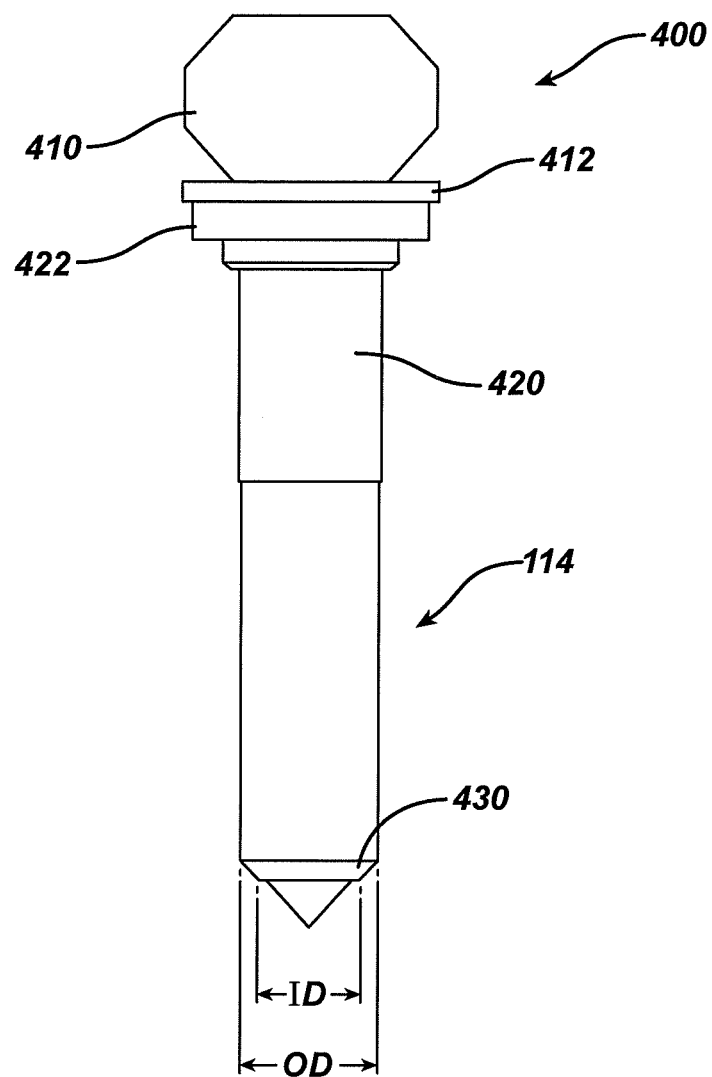
FIG. 4A is a front view of an exemplary embodiment of a surgical access device having a body and a flexible sleeve.
Figure 4B:
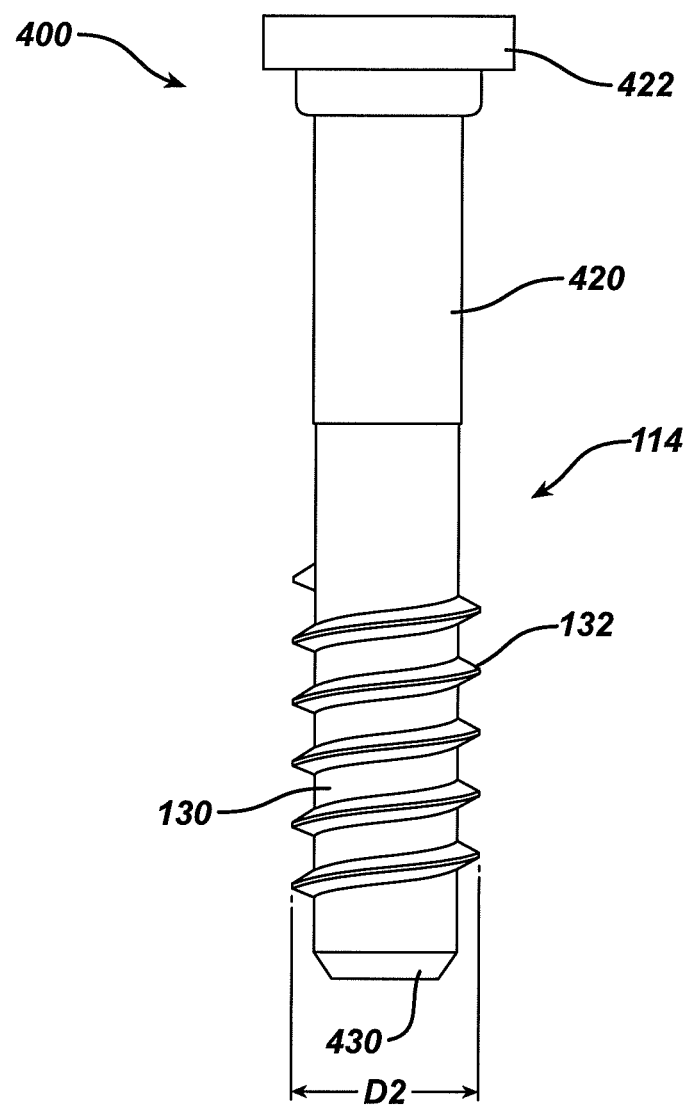
FIG. 4B is a front view of the device of FIG. 4B, in the compressed condition.

In another embodiment, shown in FIGS. 4A and 4B, a device 400 is provided having a substantially rigid collar 420 disposed adjacent to the flexible sleeve 114. The device 400 can also include a distal ring 430 coupled to the distal end of the flexible sleeve 114. A bore can be formed through the rigid collar 420, the flexible sleeve 114, and the distal ring 430 adapted for receiving a body 410. The body 410 can be any device or surgical tool known in the art, and in the illustrated embodiment, the body 410 is an obturator. In an exemplary embodiment, the body 410 can include a flange 412 configured to be disposed adjacent to a proximal flange 422 on the rigid collar 420 when the body 410 is disposed within the bore. The body 410 can have an outer diameter OD that is larger than an inner diameter ID of the distal ring 430 so that the body 410 can be contained within the bore while being prevented from passing through the distal ring 430. When the body 410 is contained within the bore, the flexible sleeve 114 is stretched so that the flexible sleeve 114 has a relatively smooth outer surface 132, as shown in FIG. 4A. When the body 410 is removed from the bore, the flexible sleeve 114 returns to its natural state in which it is compressed between the distal ring 430 and the rigid collar 420, causing protrusion 130 to form in the outer surface 132. In the illustrated embodiment, the protrusions 130 are in the form of threads.

In an exemplary embodiment, in use, the device 400 can be inserted into an incision in a patient with the body 410 contained within the bore. The body 410 causes the flexible sleeve 114 to be stretched such that the outer surface 132 of the flexible sleeve 114 is relatively smooth in an insertion condition, allowing the device 400 to be inserted with minimal tissue damage. After the device 400 is placed as needed within the patient, the body 410 can be removed from the bore, thereby causing the flexible sleeve 114 to be compressed between the proximal collar 420 and the distal ring 430 in a compressed condition. As the flexible sleeve 114 is compressed, protrusions 130 form on the outer surface 132 of the flexible sleeve 114 to engage and form a seal with the surrounding tissue. Surgical instruments can be inserted and removed through the bore in the elongate surgical access member 102 to perform surgical procedures as needed. At a point in time when the device 400 is no longer needed within the patient, the body 410 can be inserted into the bore, thereby moving the distal ring 430 distally and removing the compression from the flexible sleeve 114 so that the protrusions 130 are removed from the outer surface 132. The flexible sleeve 114 disengages from a seal with the surrounding tissue as the compression is removed, and the device 400 can then be removed from the incision with minimal tissue damage.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Preferably, the devices described herein will be processed before surgery. First, a new or used device is obtained and if necessary cleaned. The device can then be sterilized. In one sterilization technique, the device is placed in a closed and sealed container, such as a plastic or TYVEK bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility. It is preferred that the device is sterilized. This can be done by any number of ways known to those skilled in the art including beta or gamma radiation, ethylene oxide, or steam.

One skilled in the art will appreciate further features and advantages based on the above-described embodiments. Accordingly, the application is not to be limited by what has been particularly shown and described, except as indicated by the appended claims. All publications and references cited herein are expressly incorporated herein by reference in their entirety.

What is claimed is:

1. A method for providing instrument access within a patient, comprising:
    inserting a cannula assembly into an incision in a patient, the cannula assembly including an elongate surgical access member with a bore formed therethrough configured to receive a surgical tool and a tubular flexible sleeve surrounding the elongate surgical access member;
    during the step of inserting the cannula assembly into the incision the tubular flexible sleeve being configured in an insertion condition in which the tubular flexible sleeve has a relatively smooth exterior surface; and
    after inserting the cannula assembly into the incision, applying a compressive force axially to the flexible sleeve to move the flexible sleeve from the insertion condition to a compressed condition in which the exterior surface of the flexible sleeve includes surface features which extend radially outward from the elongate surgical access member at a plurality of axial locations along a length of the flexible sleeve to form a seal with tissue along the length of the flexible sleeve at the incision.

2. The method of claim 1, wherein an outer diameter of the flexible sleeve is greater in the compressed condition than in the insertion condition.

3. The method of claim 1, further comprising inserting at least one surgical tool through the bore in the member to effect a surgical procedure.

4. The method of claim 1, wherein the compressive force is applied by sliding a member distally relative to the elongate surgical access member.

5. The method of claim 1, wherein the compressive force is applied by rotating a threaded member along complimentary threads on the elongate surgical access member.

6. The method of claim 1, wherein the compressive force is applied by rotating at least one camming member.

7. The method of claim 1, wherein the compressive force is applied by withdrawing a surgical tool from the elongate surgical access member and the flexible sleeve.

8. The method of claim 7, wherein the compressed condition is the natural state of the flexible sleeve.

* * * * *